United States Patent [19]

Matsuo et al.

[11] Patent Number: 5,475,089

[45] Date of Patent: Dec. 12, 1995

[54] THROMBOLYTIC PEPTIDE, PRODUCTION THEREOF, AND THROMBOLYTIC AGENT

[75] Inventors: Osamu Matsuo, Ohsaka; Masashi Sakai, Tokyo; Kisaku Shimura, Tokyo; Hiroshi Sansawa, Tokyo; Tsunekazu Watanabe, Tokyo; Tsuneo Matsumoto, Tokyo; Yoshiyuki Shishido, Tokyo; Shusuke Hashimoto, Tokyo; Teruo Yokokura, Tokyo; Masaharu Onoue, Tokyo; Tomoyuki Sako, Tokyo, all of Japan

[73] Assignee: Kabushiki Kaisha Yakult Honsha, Tokyo, Japan

[21] Appl. No.: 75,545

[22] PCT Filed: Dec. 17, 1991

[86] PCT No.: PCT/JP91/01722

§ 371 Date: Jun. 14, 1993

§ 102(e) Date: Jun. 14, 1993

[87] PCT Pub. No.: WO92/11356

PCT Pub. Date: Jul. 9, 1992

[30] Foreign Application Priority Data

Dec. 17, 1990 [JP] Japan .................................. 2-411063

[51] Int. Cl.⁶ .......................... A61K 38/43; C07K 14/00
[52] U.S. Cl. .......................................................... 500/350
[58] Field of Search ............................... 530/350; 514/12

[56] References Cited

FOREIGN PATENT DOCUMENTS 0337817 10/1989 European Pat. Off. .
265033 10/1989 Japan .

OTHER PUBLICATIONS

Matsuo Osamu, Blood, vol. 76, No. 5, pp. 295–929, Sep. 1990.

Z. Bakteriol. Infekt. Hyg., I Abt., Suppl. 5, (1976) T. Makino et al., "Studies on Staphylokinase", pp. 539–547.

Biochimica et Biophysica ACTA, vol. 522, (1978), T. Makino "Proteolytic Modification of Staphylokinase", pp. 267–269.

*Primary Examiner*—Michael G. Wityshyn
*Assistant Examiner*—C. Sayala
*Attorney, Agent, or Firm*—Keck, Mahin & Cate

[57] ABSTRACT

A thrombolytic peptide composed of 136 amino acids residues, which has little problems of antigenicity and is efficacious in only small doses as compared with staphylokinase (SAK). This peptide is obtained by cleaving amino acids or peptides which do not affect the activity of SAK by using a trypsin protease. In particular, SAK-11, which is obtained by cleaving a peptide composed of ten amino acid residues at the N-terminal of SAK, is superior to SAK in the fibrinolysis, plasminogen activation, and fibrin specificity.

23 Claims, 7 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 163 amino acids
( B ) TYPE: amino acid
( C ) STRANDEDNESS: unknown
( D ) TOPOLOGY: linear ( i i ) MOLECULE TYPE: peptide ( x i ) SEQUENCE DESCRIPTION: SEQ ID NO: 1:

Met Leu Lys Arg Ser Leu Leu Phe Leu Thr Val Leu Leu Leu Leu Phe
         -25                    -20                    -15

Ser Phe Ser Ser Ile Thr Asn Glu Val Ser Ala Ser Ser Ser Phe Asp
     -10                -5                  1                   5

-continued

| Lys | Gly | Lys | Tyr | Lys 10 | Lys | Gly | Asp | Asp | Ala 15 | Ser | Tyr | Phe | Glu | Pro 20 | Thr |
| Gly | Pro | Tyr | Leu 25 | Met | Val | Asn | Val | Thr 30 | Gly | Val | Asp | Gly | Lys 35 | Gly | Asn |
| Glu | Leu | Leu 40 | Ser | Pro | His | Tyr | Val 45 | Glu | Phe | Pro | Ile | Lys 50 | Pro | Gly | Thr |
| Thr | Leu 55 | Thr | Lys | Glu | Lys | Ile 60 | Glu | Tyr | Tyr | Val | Glu 65 | Trp | Ala | Leu | Asp |
| Ala 70 | Thr | Ala | Tyr | Lys | Glu 75 | Phe | Arg | Val | Val | Glu 80 | Leu | Asp | Pro | Ser | Ala 85 |
| Lys | Ile | Glu | Val | Thr 90 | Tyr | Tyr | Asp | Lys | Asn 95 | Lys | Lys | Lys | Glu | Glu 100 | Thr |
| Lys | Ser | Phe | Pro 105 | Ile | Thr | Glu | Lys | Gly 110 | Phe | Val | Val | Pro | Asp 115 | Leu | Ile |
| Glu | His | Ile 120 | Lys | Asn | Pro | Gly | Phe 125 | Asn | Leu | Ile | Thr | Lys 130 | Val | Val | Ile |
| Glu | Lys 135 | Lys | | | | | | | | | | | | | |

( 2 ) INFORMATION FOR SEQ ID NO: 2:

( i ) SEQUENCE CHARACTERISTICS:
( A ) LENGTH: 126 amino acids
( B ) TYPE: amino acid
( C ) STRANDEDNESS: unknown
( D ) TOPOLOGY: linear ( i i ) MOLECULE TYPE: peptide ( x i ) SEQUENCE DESCRIPTION: SEQ ID NO: 2:

| Lys | Gly | Asp | Asp | Ala 5 | Ser | Tyr | Phe | Glu | Pro 10 | Thr | Gly | Pro | Tyr | Leu 15 | Met |
| Val | Asn | Val | Thr 20 | Gly | Val | Asp | Gly | Lys 25 | Gly | Asn | Glu | Leu | Leu 30 | Ser | Pro |
| His | Tyr | Val 35 | Glu | Phe | Pro | Ile | Lys 40 | Pro | Gly | Thr | Thr | Leu 45 | Thr | Lys | Glu |
| Lys | Ile 50 | Glu | Tyr | Tyr | Val | Glu 55 | Trp | Ala | Leu | Asp | Ala 60 | Thr | Ala | Tyr | Lys |
| Glu 65 | Phe | Arg | Val | Val | Glu 70 | Leu | Asp | Pro | Ser | Ala 75 | Lys | Ile | Glu | Val | Thr 80 |
| Tyr | Tyr | Asp | Lys | Asn 85 | Lys | Lys | Lys | Glu | Glu 90 | Thr | Lys | Ser | Phe | Pro 95 | Ile |
| Thr | Glu | Lys | Gly 100 | Phe | Val | Val | Pro | Asp 105 | Leu | Ile | Glu | His | Ile 110 | Lys | Asn |
| Pro | Gly | Phe 115 | Asn | Leu | Ile | Thr | Lys 120 | Val | Val | Ile | Glu | Lys 125 | Lys | | |

THROMBOLYTIC PEPTIDE, PRODUCTION THEREOF, AND THROMBOLYTIC AGENT

TECHNICAL FIELD

This invention relates to a thrombolytic agent obtained from staphylokinase which are effective for curing myocardial infarction, walnut brain, arteriosclerosis and the like, by cleaving therefrom moieties which do not affect its activity.

BACKGROUND ART

Staphylokinase (hereinafter abbreviated as SAK) has no protease activity in itself, but is a kind of plasminogen activator similar to streptokinase (hereinafter abbreviated as SK) in that its complex with plasminogen or plasmin activates plasminogen. SAK has a molecular weight of about 15,000 and a size which is not greater than ⅓ of the size of SK. Since the genes have been cloned and their DNA sequences have been elucidated, it is considered that SAK is an appropriate substance for analyzing the action mechanism on a molecular level. The inventors of this application have proposed a method for collecting SAK accumulated in coliform bacilli which are integrated with SAK genes and cultivated (Japanese Patent Laid-open No. 58-67181). A major proportion of SAK obtained by the method is composed of a peptide which consists of 136 amino acid residues SEQ ID NO: 1 (Sako, T., Eur. J. Biochem., 149, 557–563(1985)).

It has been found that the action mechanism of SAK is different from that of SK. Especially, it has been confirmed that unlike SK, SAK has such a characteristic feature that the activity is increased in the presence of fibrin (i.e. fibrin specificity) and, thus, functions as a good thrombolytic agent (Japanese Patent Laid-open No. 63-90252). Also, in order to improve the delayed reactivity of SAK, there has been proposed a thrombolytic agent in which a complex of SAK and plasminogen (or fibrin) is preformed (Japanese Patent Laid-open No. 1-13044).

SAK composed of a peptide which consists of 136 amino acid residues obtained by the above-mentioned method is advantageous in that its molecular weight is smaller than other thrombolytic agents hitherto employed, ensuring good penetration into thrombi, coupled with another advantage that mass production by a simple manner is possible. This results in a better economy than in the case of other thrombolytic agents.

Although SAK composed of a peptide which consists of 136 amino acid residues has good characteristics as stated above, a smaller molecular weight is more preferable to prevent the occurrence of problems on antigenicity and dosage, etc.

DISCLOSURE OF THE INVENTION

The object of the present invention is to improve SAK composed of a peptide which consists of 136 amino acid residues, and to provide a thrombolytic agent, which is capable of preventing the occurrence of the problems on the antigenicity or immunogenicity with the reduced dosage.

To accomplish the above object, a thrombolytic agent according to one aspect of the present invention contains a peptide residue having at least an amino acid sequence set forth in SEQ ID NO: 2.

In more detail, according to an embodiment of the present invention, the thrombolytic agent contains as its effective ingredient the peptide residue obtained from SAK by cleaving off a moiety including an amino acid or a peptide which does not affect the activity of said SAK. More preferably, the thrombolytic agent contains as its effective ingredient the peptide residue obtained from said SAK by cleaving off a peptide composed of ten amino acid residues at the N-terminal of said SAK through a treatment process for said SAK with a trypsin protease.

More particularly, it has been found that such a peptide residue as set forth above has the thrombolytic action better than the original SAK.

In the present invention, studies have been made on the cleaving, from SAK composed of a peptide which consists of 136 amino acid residues, of the moiety having no affect on the activity of SAK by using various types of protease. As a result, it has been found that a peptide (hereinafter referred to simply as SAK-11) which is obtained by cleaving from SAK a peptide consisting of ten amino acids at the N-terminal (i.e. Ser Ser Ser Phe Asp Lys Gly Lys Tyr Lys) is equivalent to SAK consisting of 136 amino acids (peptides) with respect to the fibrinolysis, plasminogen activity, fibrin specificity and the like properties and is better in several respects. SAK-11 in which the peptide consisting of ten amino acids at the N-terminal is cleft from the original SAK serves as a thrombolytic agent which is more preferable to prevent the occurrence of the problem on antigenicity with smaller dosage than SAK.

It has been found that SAK-11 is produced by acting a protease, particularly a trypsin protease on SAK. Especially, it has been found that when plasminogen is used, SAK-11 is formed without formation of impurities and that other decomposition does not occur. It will be noted that in place of plasminogen, plasmin which is an activator of plasminogen may be likewise used.

Other typical trypsin proteases usable in the present invention include trypsin, lysyl endopeptitase, enterokinase, thrombin, blood coagulation factor VIIa, blood coagulation factor IXa, blood coagulation factor Xa, blood coagulation factor XIa, blood coagulation factor XIIa, horseshoe crab coagulase, urokinase, prourokinase, tissue plasminogen activator, high molecular weight kininogen, low molecular weight kininogen, cathepsin B, plasma kallikrein, pancreatic kallikrein, and the like. Besides, sofar as they develop their activity in the reaction system of the present invention, zymogens (enzyme precursors) may also be used.

As stated hereinabove, SAK-11 can be produced by the action of various types of trypsin proteases (by cutting the C-end side of the basic amino acids). In some cases, not only SAK-11, but also impurities may be formed. In the case, isolation and purification will be subsequently required.

The utilization of a fixed enzyme makes it possible to simplify the purification operation (such as removal of the enzyme) and to repeatedly use the enzyme.

Thus, SAK-11 in which the peptide consisting of ten amino acids at the N-terminal is removed from SAK has a number of characteristic features such as a lowering of antigenicity, an improvement of stability, simplification of metabolic tests and the like.

As stated before, in the practice of the invention, studies have been made on the cleaving, from SAK composed of a peptide which consists of 136 amino acid residues, of amino acids having no affect on SAK activity by use of various types of proteases. As a result, there has been obtained a thrombolytic agent comprising peptide as shown by SEQ ID NO: 2, which has a number of characteristic features such as a lowering of antigenicity, an improvement of stability, simplification of metabolic tests and the like.

More particularly, the thrombolytic agent comprising as its effective ingredient a specific 126 amino acid residues (peptide, SAK-11) obtained by cleaving from an original SAK a peptide which consists of ten amino acid residues at the N-terminal of the SAK is superior to the original SAK consisting of 136 amino acids (peptide) with respect to the activities such as fibrinolysis, plasminogen activation reaction, fibrin specificity and the like.

As stated hereinabove, the thrombolytic agent containing SAK-11 which is obtained by cleaving a peptide consisting of ten amino acids at the N-terminal from SAK has a number of characteristic properties such as lower antigenicity, improved stability, simplification of metabolic tests, etc.

BEST MODE FOR CARRYING OUT THE INVENTION

Figure 1:
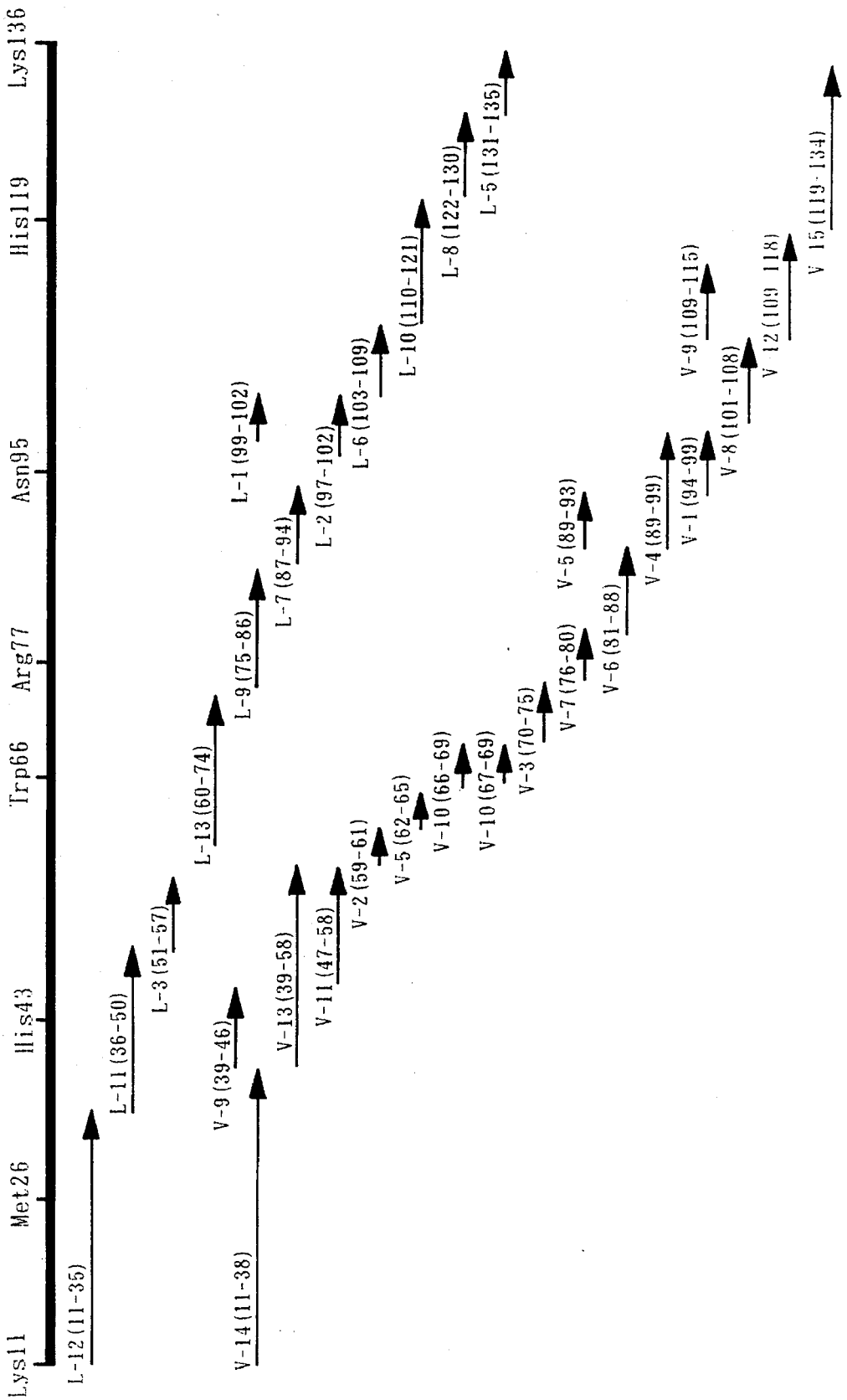
FIG. 1 is a peptide map showing a conformation of all fractionated peptides of collected SAK-11.

1. Reactions With Various Types of Enzymes:

SAK was reacted with various types of enzymes to determine the resultant reaction products. The results are shown in Table 1. As shown in Table 1, trypsin proteases such as plasminogen, plasmin, trypsin, and lysyl endopeptidase could yield SAK-11 in which ten amino acids at the N-terminal were eliminated from SAK consisting of 136 amino acids (peptides). Especially, any impurity was not formed when using plasminogen or plasmin, thereby producing SAK-11 in an effective manner.

TABLE 1

| Protease | Main Reaction Product | Impurities |
|---|---|---|
| Plasminogen | SAK-11 | no |
| Plasmin | SAK-11 | no |
| Trypsin | SAK-11 | yes |
| Lysyl endopeptidase | SAK-11 | yes |
| Pepsin | mixture | yes |
| Chimotrypsin | mixture | yes |
| Protinase K | mixture | yes |
| V8 Protease | mixture | yes |
| Crostripain | mixture | yes |

2. Procedure Using Reaction With Human Plasminogen:

A human plasminogen solution in a corresponding amount of 0.01 mg (0.133 CU) was added to 1.0 ml of SAK solution (4 mg/ml) in a 10 mM sodium phosphate buffer (pH 8.0) and incubated at 37° C. for 3 hours. The reaction product was subjected to SDS polyacrylamide electrophoretic analysis, revealing the conversion of all the SAK into SAK-11.

The reaction product was subjected to purification through a positive ion exchange chromatography using an S-Sepharose column to obtain SAK-11, which was confirmed to be SAK-11 in view of the N-terminal amino acid sequence.

As will be set forth hereinafter, this product exhibited activities equal to or better than SAK consisting of 136 amino acids as calculated by moles.

3. Utilization of Fixed Plasminogen:

Human plasminogen was coupled with a commercially available BrCN-activated Sepharose 4B to obtain fixed plasminogen (Plasminogen-Sepharose 4B). 0.2 ml of the fixed plasminogen was filled in a 1 ml plastic injection syringe and washed twice with 0.5 ml of buffer A, followed by further addition of 0.05 ml of SAK (0.2 mg/0.05 ml), washing four times with 0.5 ml of buffer A, and elution with 0.5 ml of buffer B.

Buffer A: 0.01M phosphate buffer (pH 7.0)
Buffer B: 0.1M citrate buffer (pH 4.25)+0.4M NaCl As a consequence, it was confirmed through electrophoresis that SAK was collected in a column-adsorbed fraction and converted to SAK-11.

4. Determination of Amino Acid Sequence of SAK-11:

Using a peptide-matching technique, the amino acid sequence was exactly determined. The proteases used were lysyl endopeptidase (Achromobacter Protease I, available from Wako Junyaku Ind. Co., Ltd.) and V8 protease (Takara Brewery Co., Ltd.). Lysyl endopeptidase and V8 protease were, respectively, diluted with water make concentrations of 100 μg/ml and 200 μg/ml.

In the case of the treatment with lysyl endopeptidase, the enzymatic reaction was effected in such a manner that 5 μg of SAK-11 and 0.1 micrograms of the enzyme were added to 20 microliters of a reaction solution containing 20 mM tris-hydrochloride (pH 9.5), followed by incubation at 37° C. for 6 hours. With V8 protease, 5 micrograms of SAK-11 and 0.67 micrograms of the enzyme were added to 20 microliters of a reaction solution containing 50 mM of ammonium hydrogen carbonate (pH 7.9) and 1 mM of EDTA, followed by incubation at 37° C. for 24 hours.

After completion of the enzymatic reactions, the respective solutions were each subjected to the HPLC procedure to isolate peptide fragments. The HPLC system used was a combination of LC-6A System, made by Shimadzu Ltd., (two LC-6A units, one SPD-6AV unit, one C-R3A unit and one SCL-6A unit), ERC-3322 Degussor, available from Elmer Co., Ltd., and AS-100T Auto Sampler, available from Bio-Rad Co., Ltd. In the system, the absorbance at 210 nm of the elute was measured in a full scale of 0.02. The column used for the isolation was μ BOND ASPHERE C18 column (size of 5 μm, pore size of 300 angstroms, 3.9 mm×150 mm), available from Japan Waters Co., Ltd.

The isolation through HPLC was made in the following manner: 280 microliters of solvent A (water containing 0.1% of TFA) was added to 20 microliters (containing 5 micrograms of SAK-11) of the sample obtained after the enzymatic reaction to make a total amount of 300 microliters; 280 microliters of the mixture was applied so that a linear concentration gradient procedure using two solvents, i.e. solvent A and solvent B (acetonitrile containing 0.1% TFA), was made at a flow rate of 1 ml/minute. The concentration gradient conditions are selected from those conditions indicated in Table 2 below.

TABLE 2

| Gradient-1 | | Gradient-2 | | Gradient-3 | |
|---|---|---|---|---|---|
| 0 min | 5% B | 0 min. | 3% B | 0 min. | 2% B |
| 5 min | 5% B | 5 min. | 3% B | 5 min. | 2% B |
| 55 min | 50% B | 55 min. | 45% B | 55 min. | 45 % B |
| 60 min | 70% B | 60 min. | 70% B | 60 min. | 70 % B |
| 65 min | 70% B | 65 min. | 70% B | 65 min. | 70 % B |
| 65.01 min. | 5% B | 65.01 min. | 3% B | 65.01 min. | 2% B |
| 80.01 min. | 5% B | 79 min. | 3% B | 79 min. | 2% B |
| 80.01 min. | STOP | 79.01 min. | STOP | 79.01 min. | STOP |

From the reaction solution obtained after the treatment with lysyl endopeptitase, there were isolated peaks ranging from L-1 to L-13 through the HPLC analysis. Likewise, from the reaction solution obtained after the treatment with V8 protease, there were isolated fractions of peaks ranging from V-1 to V-15. The resultant respective peptide fractions were each subjected to determination of the amino acid sequence using Protein Sequencer, available from Applied Bio System Co., Ltd.

The results of the amino acid sequence (SEQ ID NO: 1) of the peptides in the respective fractions are as shown in Table 3. In addition, FIG. 1 shows a peptide map which exhibits conformations of the peptides in all fractions of collected SAK-11. As shown in FIG. 1, all amino acid sequences except for the C-terminal amino acid residues of SAK-11 are determined.

TABLE 3

| No. | Position | Amino Acid Sequence (SEQ ID NO: 1) |
|---|---|---|
| L-1 | 99-102 | Glu Glu Thr Lys |
| L-2 | 97-102 | Lys Lys Glu Glu Thr Lys |
| L-3 | 51-57 | Pro Gly Thr Thr Leu Thr Lys |
| L-4 | — | — |
| L-5 | 131-135 | Val Val Ile Glu Lys |
| L-6 | 103-109 | Ser Phe Pro Ile Thr Glu Lys |
| L-7 | 87-94 | Ile Glu Val Thr Tyr Tyr Asp Lys |
| L-8 | 122-130 | Asn Pro Gly Phe Asn Leu Ile Thr Lys |
| L-9 | 75-86 | Glu Phe Arg Val Val Glu Leu Asp Pro Ser Ala Lys |
| L-10 | 110-121 | Gly Phe Val Val Pro Asp Leu Ser Glu His Ile Lys |
| L-11 | 36-50 | Gly Asn Glu Leu Leu Ser Pro His Tyr Val Glu Phe Pro Ile Lys |
| L-12 | 11-35 | Lys Gly Asp Asp Ala Ser Tyr Phe Glu Pro Thr Gyl Pro Tyr Leu Met Val Asn Val Thr Gly Val Asp Gly Lys |
| L-13 | 60-74 | Ile Glu Tyr Tyr Val Glu Trp Ala Leu Asp Ala Thr Ala Tyr Lys |
| V-1 | 94-99 | Lys Asn Lys Lys Lys Glu |
| V-2 | 59-61 | Lys Ile Glu |
| V-3 | 70-75 | Ala Thr Ala Tyr Lys Glu |
| V-4 | 89-99 | Val Thr Tyr Tyr Asp Lys Asn Lys Lys Lys Glu |
| V-5 | 62-65 | Tyr Tyr Val Glu |
| V-6 | 81-88 | Leu Asp Pro Ser Ala Kys Ile Glu |
| V-7 | 76-80 | Phe Arg Val Val Glu |
| V-8 | 101-108 | Thr Lys Ser Phe Pro Ile Thr Glu |
| V-9 | 39-46 | Leu Leu Ser Pro His Tyr Val Glu |
| | 109-115 | Lys Gly Phe Val Val Pro Asp |
| V-10 | 66-69 | Trp Ala Leu Asp |
| | 67-69 | Ala Leu Asp |
| V-11 | 47-58 | Phe Pro Ile Lys Pro Gly Thr Thr Leu Thr Lys Glu |
| V-12 | 109-118 | Lys Gly Phe Val Val Pro Asp Leu Ser Glu |
| V-13 | 39-58 | Leu Leu Ser Pro His Tyr Val Glu Phe Pro Ile Lys Pro Gly Thr Thr Leu Thr Lys Glu |
| V-14 | 11-38 | Lys Gly Asp Asp Ala Ser Tyr Phe Glu Pro Thr Gly Pro Tyr Leu Met Val Asn Val Thr Gly Val Asp Gly Lys Gly Asn Glu |
| V-15 | 119-134 | His Ile Lys Asn Pro Gly Phe Asn Leu Ile Thr Lys Val Val Ile Glu |

As shown in Table 3 and FIG. 1, it has been confirmed that the sequence of SAK-11 ranging from Lys-11 to Lys-13 is completely coincident with the amino acid sequence expected from the gene sequence.

In order to elucidate the structure of the carboxyl terminal (C-terminal) of SAK-11, the following experiment was carried out. That is, 0.15 ml of a 0.1M sodium citrate buffer (pH 3.8) was added to an equal amount of an SAK-11 solution (2.4 mg/ml), followed by addition of 0.1 ml of a carboxy peptidase W (Biochem. Ind. Co.) solution (20 mg/ml) and reaction at 37 ° C. for 0, 5 and 20 hours respectively after commencement of the reaction, 0.10 ml was sampled, to which 0.01 ml of 0.1M diisopropylfluorophosphate (DFP) was added thereby stopping the reaction, then 0.29 ml of a 20 mM sodium phosphate solution was further added thereby adjusting the pH.

The resultant reaction solutions were each subjected to ultrafiltration using Centricon 10 (available from Amicon Co., Ltd.) for fractionation into a higher molecular weight fraction (>10,000 in molecular weight) and a lower molecular weight fraction (<10,000 in molecular Weight). The higher molecular weight fraction obtained in the respective reaction times was analyzed through cation exchange chromatography (Mono Q, PPLC System). As a result, it was found that while only peak I (unreacted SAK-11) was recognized prior to the commencement of the reaction, the peak I was reduced in intensity 5 hours after the reaction and a shifted peak II and a more shifted peak III were detected. When a reaction time of 20 hours was passed, peaks I and II were scarcely recognized and most of the peaks consisted of peak III.

In general, with cationic exchange chromatography, proteins are more likely to elude in the order of a higher isoelectric point. Moreover, the results of electrophoresis of SDS-polyacrylamide reveal that the molecular weights of the fractions of peaks I, II and III do not substantially differ from one another. In view of these facts, peaks II and III are, respectively, assumed to consist of proteins from which one or two basic amino acids are lost from that of peak I. The results of free amino acids in the lower molecular weight fraction reveal that lysin (Lys) alone appears 5 hours after the reaction and its amount is increased after 20 hours.

From the above results, it will be concluded that the sequence of the C-terminal two amino acids of SAK-11 is composed of Lys-Lys. As assumed from the DNA sequence of SAK, it has been confirmed that the amino acid sequence is one in which a peptide composed of the N-terminal ten amino acids is eliminated from SAK without any other amino acid modification and any loss of other amino acids. In SEQ ID NO: 2, all the amino acid sequence of SAK-11 is shown.

5. Thrombolytic Test of SAK-11 (Rabbit Thrombus Model):

For the purpose of assessing the medical efficacy of the thrombolytic action of SAK-11, a study was made on a rabbit vena jugularis thrombus model.

The test animals used were New Zealand white male rabbits (Kbl:NZW), each having a weight not smaller than 2.8 Kg. Six rabbits in each group (eleven rabbits only in a control group) were used for the test. A sample which was dosed to individual animals was prepared as a physiological saline solution which finally contained 0.003 % of Tween 80 and 3 mM of a phosphate buffer and wherein SAK-11 was contained in an amount from 0.15 to 2.1 mg/kg as a dosage.

The thrombi were formed as follows. Initially, a syringe (1 ml) filled with a thrombin solution (25 mM CaCl2 solution with 3U/ml) was connected to an indwelling needle to wash twice a blood vessel used to prepare thrombi. Subsequently, fresh blood was collected in another syringe (1 ml) from a catheter set in the femoral vein. About 0.25 ml of the fresh blood was quickly injected into the blood vessel from the indwelling needle, followed by allowing to stand for 30 minutes while keeping the needle to set in the syringe. After 30 minutes, the syringe and the needle were removed from the anterior facial vein, followed by ligation. Clamps set at opposite side of the vein for the preparation of thrombi were removed so that the blood stream cycle was re-started to complete the preparation of a rabbit jugular vena thrombus model. After the operation, the cut portions were applied with cut cotton impregnated with physiological saline in order to prevent drying.

The sample was so dosed that immediately after the blood passage for preparing the thrombi, physiological saline solutions containing different concentrations of SAK-11 and a physiological saline containing Tween 80 and a phosphate buffer alone as a control were, respectively, subjected to phleboclysis by means of a syringe pump through the auricular vein at a side opposite to the thrombus-prepared site.

The dosage rate was such that 2 ml of the solution was subjected to bolus administration in one minute at a flow rate of 120 ml/hour and then the balance of 18 ml was subjected to drip phleboclysis at a flow rate of 4.5 ml/hour in 4 hours. In order to inhibit the growth of the prepared, experimental thrombi, a heparin solution (10 U/ml, available from Nobo Co., Ltd.) was intravenously injected at opposite sides of the thrombus-prepared site each in an amount of 0.5 ml. Moreover, the solution was also intravenously injected from a catheter set in the femoral vein in an amount of 0.5 ml every 30 minutes immediately after the completion of the thrmobus preparation.

Figure 2:
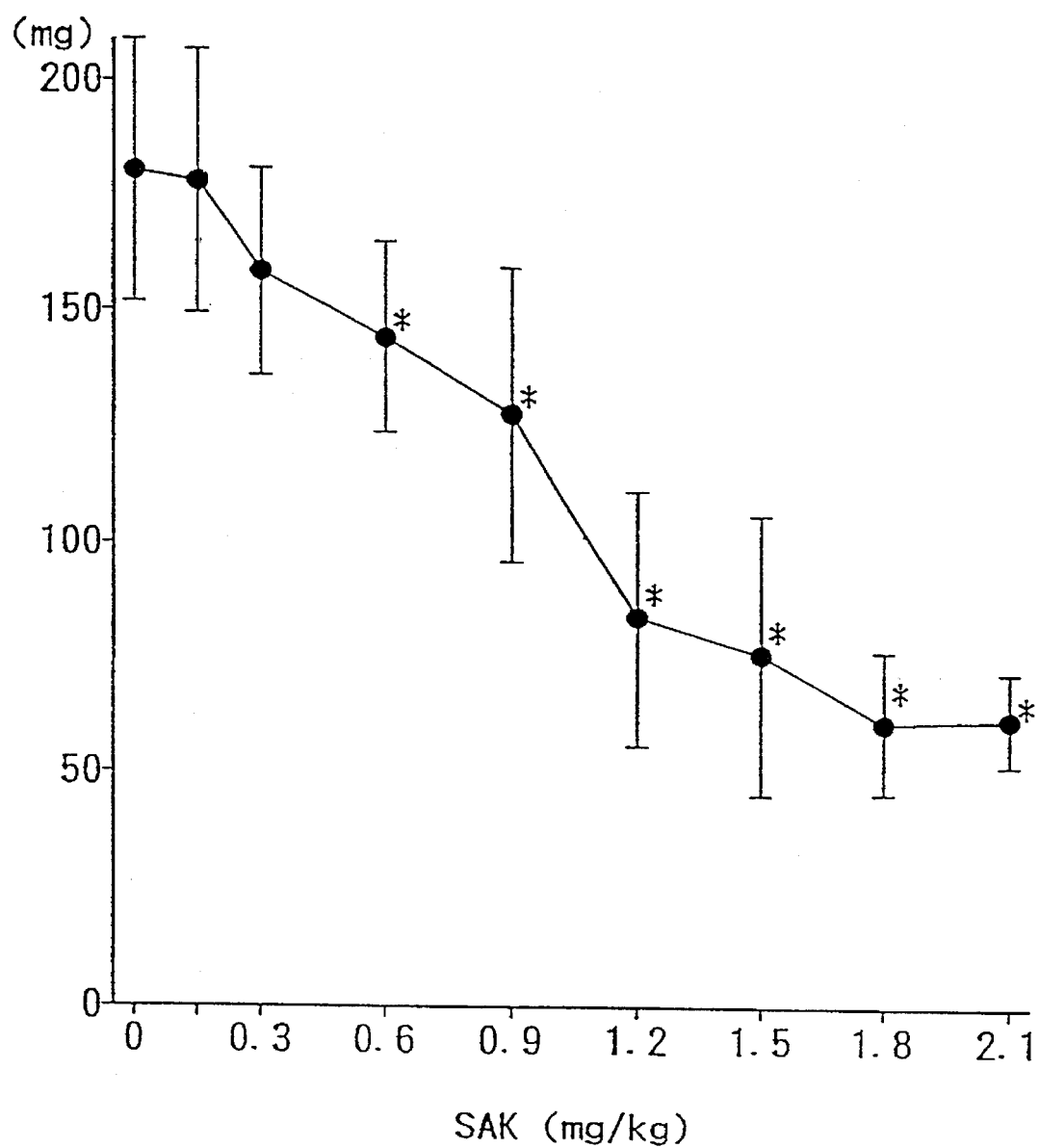
FIG. 2 is a graph showing the relation between the dosage of SAK-11 and the wet weight of thrombi.

The wet weight of the thrombi was measured as follows: immediately or six hours after the preparation of the thrombi, the blood vessel Of jugular vena was ligated at opposite sides around the thrombus-prepared site. The jugular vena in this area was extracted. The blood vessel of the thus extracted jugular vena was subjected to discission and placed in a physiological saline solution in a laboratory dish thereby washing away uncoagulated blood present in the vessel. Additional moisture deposited on the vena was removed by absorption with filter paper, followed by measurement of weight A (total weight of thrombi, vessel and ligature) by means of a balance. Thereafter, the vessel was again placed in the dish and the thrmobi present therein were washed away, followed by absorption of moisture with filter paper and measurement of weight B (total weight of the vessel and the regature). The wet weight of the thrombi was obtained by subtracting weight B from weight A. FIG. 2 is a graph showing the relation between the dosage of SAK-11 and the wet weight of the thrombi in which the ordinates indicates the wet weight of the thrombi (mg) and the abscissa indicates the dosage of SAK (mg/kg). The number of rabbits to which 0 mg of SAK was dosed was 11 and other groups each consisted of six rabbits. The respective values were an average value± standard deviation of the wet weights of thrombi.

In the above experiment, prior to the administration of SAK and 2, 4 and 6 hours after the administration, blood was drawn from individual rabbits of each group for measurement of fibrinogen in plasma.

The thus drawn plasma was isolated, and 5M s-amino-n-caproic acid was placed in each of four wells of an immuno-plate in an amount of 20 microliters per ml of the plasma. 50 microliters of a veronal buffer was added to the two wells for use as a reference. 50 microliters of 12.5 mM veronal buffer which contained 0.5 U/ml of thrombin and 12.5 mM of $CaCl_2$ was added to the other two wells. These wells were kept at 37° C. for one minutes, followed by measurement of an absorbance at 405 nm. $\Delta$ OD was obtained by subtracting the OD value of the wells to which thrombin and $CaCl_2$ were added from the OD value of the reference wells.

The variation index of fibrinogen in the plasma was determined as follows: the values of $\Delta$ OD were determined using plasmas which were gathered 0, 2, 4 and 6 hours after administration of SAK; and the values of $\Delta$ OD for the respective times were expressed by percent when the OD value of the plasma after 0 hour was taken as 100 %. The results are shown in Table 4. As shown in Table 4, the results are shown by average values ± standard deviation. The active dose of SAK was detected according to Duncan's multiple range test wherein when the risk factor is not larger than 5 %, the difference is determined as significant for each case.

As stated hereinabove, with regard to the thrombolytic action, when SAK-11 was dosed at 0.15 mg and 0.3 mg/kg, respectively, the wet weight of the thrombi was significantly reduced, depending on the dosage, relative to the control. With the group where 1.8 mg/kg was dosed, the wet weight of thrombi was 60.8±15.5 mg. The thrombolytic rate amounted to 66.2 % so that a thrombic mass was only slightly recognized at the thrombus-prepared site. The influence of SAK-11 on the fibrinogen in the rabbit plasma is such that when the dosage of SAK-11 is up to 0.6 mg/kg, little reduction in the amount of fibrinogen in the plasma was recognized, and when the dosage is not lower than 0.9 mg/kg, the reduction in amount of fibrinogen was apparently recognized.

TABLE 4

| Dosage (mg/kg) | Time After Administration of SAK (Hours) | | |
|---|---|---|---|
| | 2 | 4 | 6 |
| 0.15 | 107.6 ± 10.6 | 107.2±11.6 | 118.5±14.6 |
| 0.3 | 88.8 ± 9.4 | 89.8±7.0 | 93.5±9.7 |
| 0.6 | 86.7 ± 3.4 | 87.7±2.5 | 103.5±7.1 |
| 0.9 | 78.8 ± 4.3 | 77.9±7.9 | 88.9±6.8 |
| 1.2 | 64.6 ± 19.4 | 68.9±7.4 | 70.8±11.0 |
| 1.5 | 60.0 ± 28.0 | 69.1±5.0 | 82.0±22.8 |
| 1.8 | 73.2 ± 1.9 | 66.4±1.9 | 82.0±9.9 |
| 2.1 | 72.1 ± 8.3 | 67.1±12.5 | 85.5±26.3 |

6. Thrombolytic Test of SAK-11 (Closed Circulation Model):

Using a closed circulation model (Matsuo et al, Thromb. Res., 24, 347–358 (1985)), a human plasma thrombolytic test of SAK-11 was effected. With regard to the final concentration of SAK-11, 1/10 of the total amount was initially charged at one time so that the concentration was 2 μg/ml relative to the total amount of the circulating plasma and the balance of 9/10 was charged by use of a pump in 4 hours.

Figure 3:
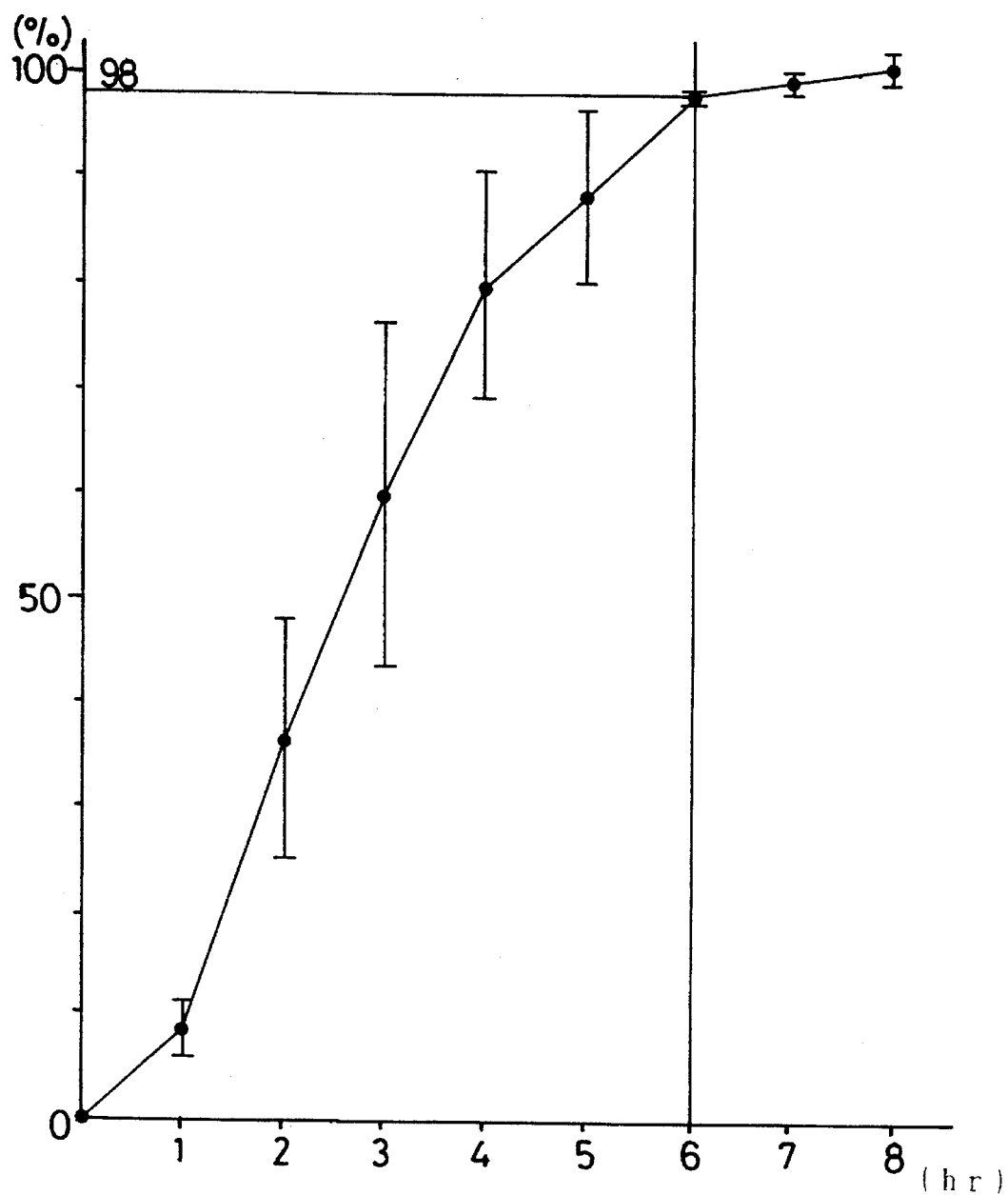
FIG. 3 is a graph showing the thrombolytic reaction in relation to the variation in time.
Figure 4:
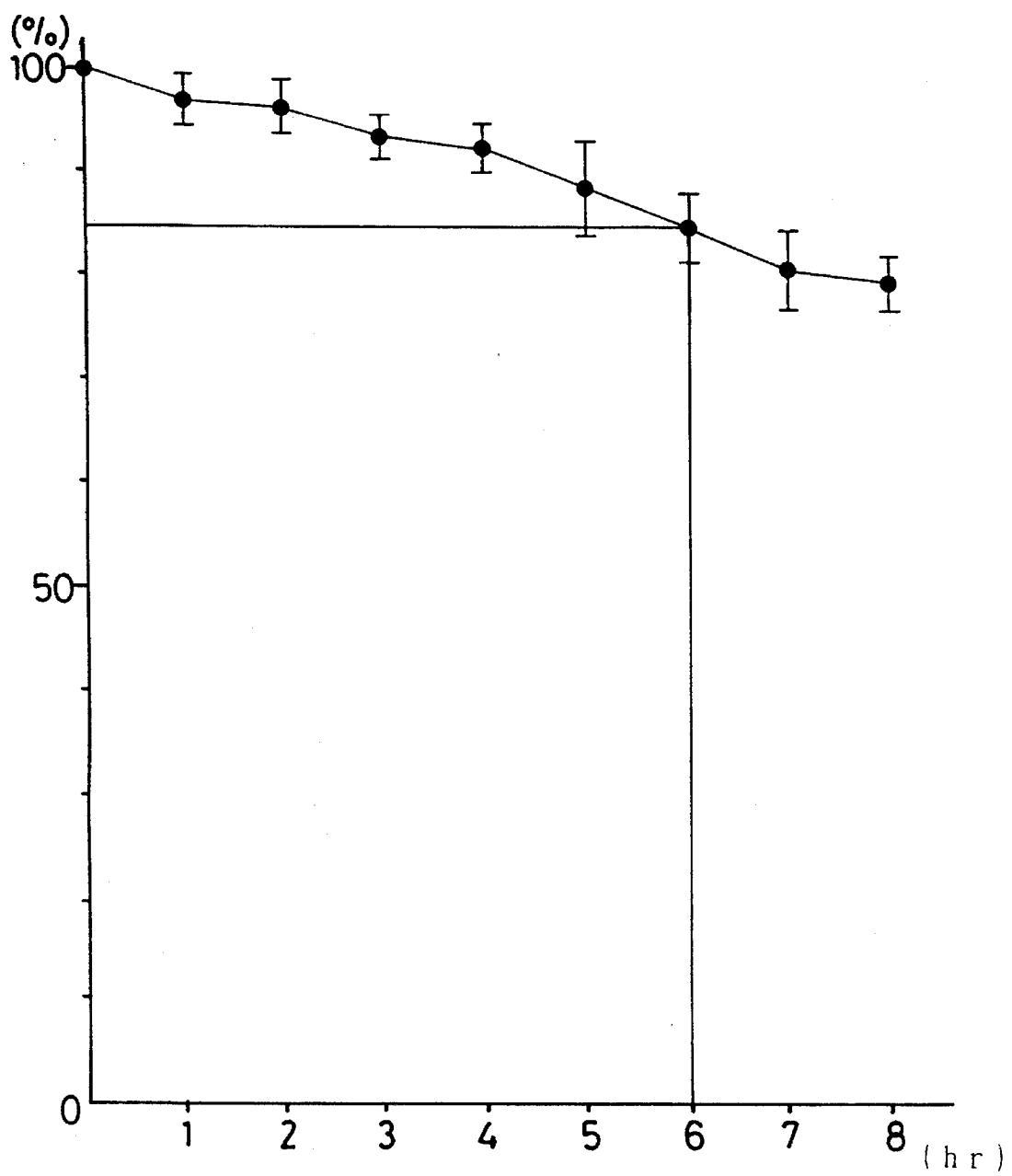
FIG. 4 is a graph showing the amount of fibrinogen left in plasma in relation to the variation in time.
Figure 5:
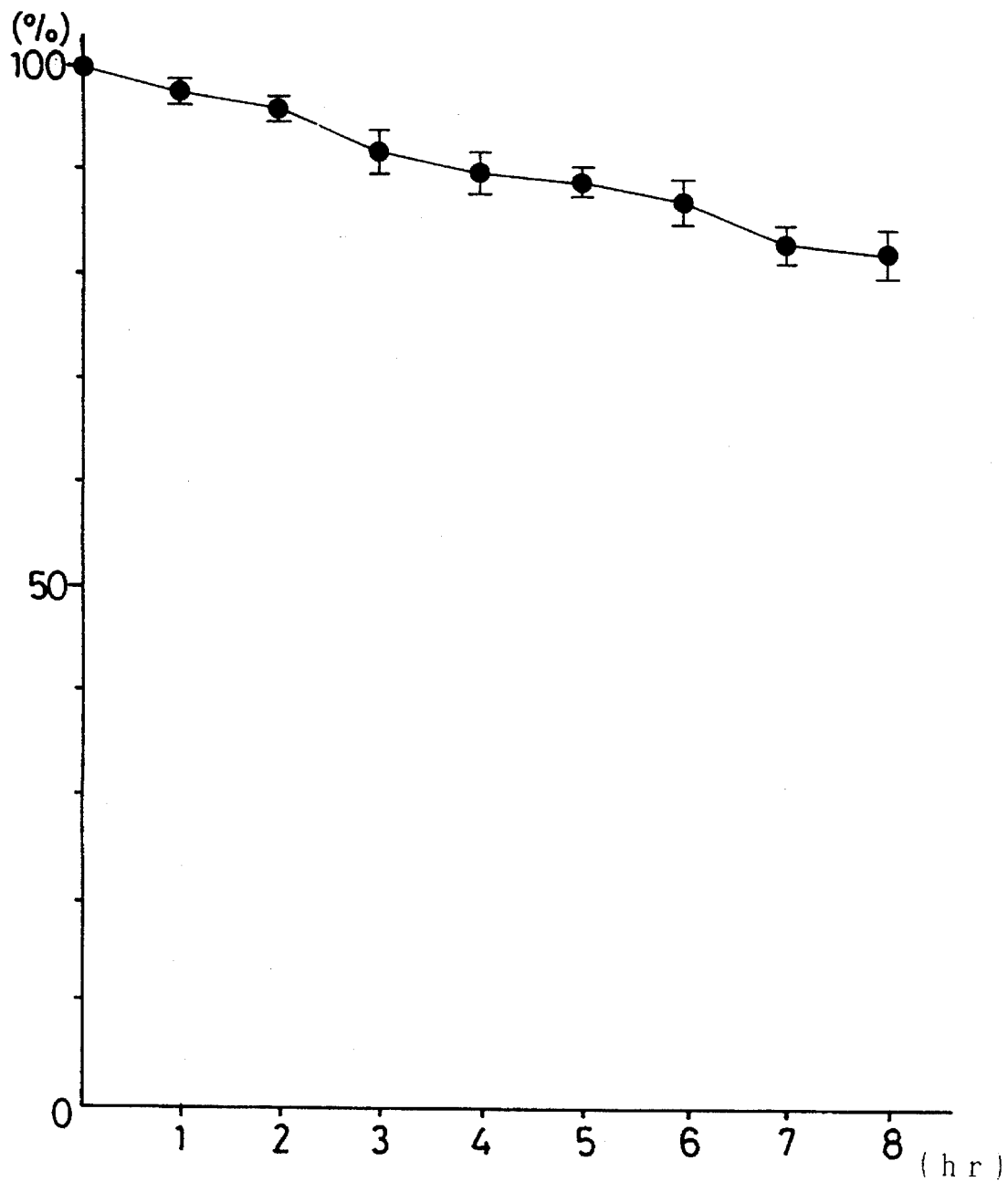
FIG. 5 is a graph showing the amount of plasminogen left in plasma in relation to the variation in time.
Figure 6:
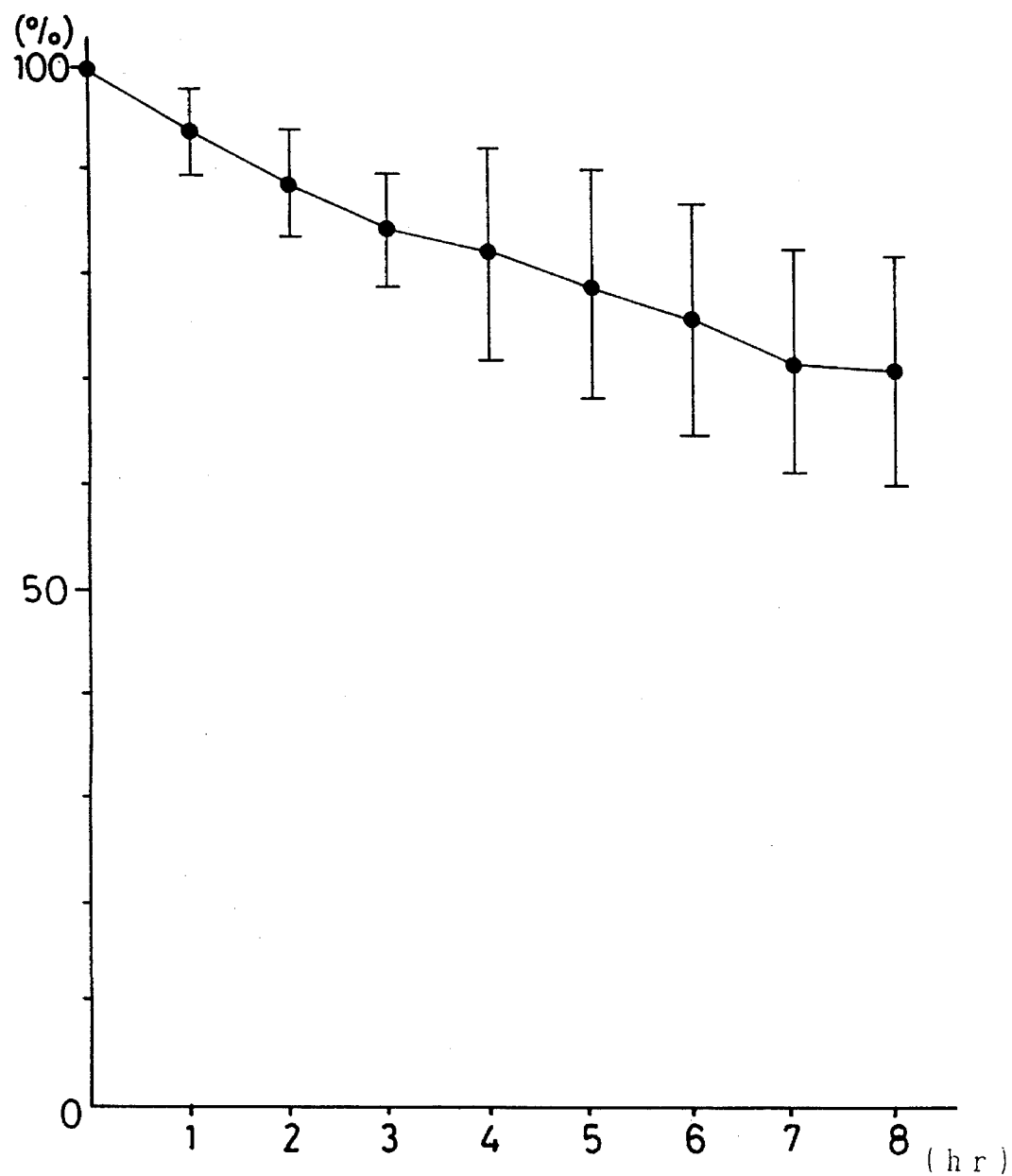
FIG. 6 is a graph showing the amount of α-plasmin inhibitor left in plasma in relation to the variation in time.

A given amount of the plasma was drawn every hour from the lower chamber of the circulation model. The thrombolytic state was assessed from the radio activity released from the thrombi. Moreover, the same sample as used above was employed to quantitatively determine the amounts of fibrinogen, plasminogen and $\alpha_2$-plasminogen inhibitor. The experiment was made using N=3, and average values and standard deviations were calculated. FIG. 3 is a graph showing the thrombolytic reaction in relation to the variation in time wherein the ordinates indicates radioactivity and the abscissa indicates time. FIG. 4 is a graph showing the content of fibrinogen left in the plasma in relation to the variation in time. FIG. 5 is a graph showing the content of plasminogen left in the plasma in relation to the variation in time. FIG. 6 is a graph showing the content of $\alpha_2$-plasminogen inhibitor left in the plasma in relation to the variation in time. In these figures, the ordinates indicates the content by percent of each of fibrinogen, plasminogen and G 2-plasminogen inhibitor.

As shown in FIGS. 3 to 6, the thrombi are efficiently dissolved as time passes, and the fundamental properties of thrombolytic agents are properly shown. At the same time, the fibrinolysis in the circulating plasma is slight in degree, and the thrombolytic characteristic (value at 16 hours of (thrombolytic percent/fibrinolytic percent)) is 6.32 which is greater than 1, showing tissue plasminogen activator (tPA) properties.

7. Comparison in fibrin specificity between SAK-11 and SAK By Synthetic Substrate Method:

Staphylokinase (SAK) and SAK-11 are, respectively, a plasminogen activator which develops an efficacy by forming a complex with plasminogen and have high fibrin specificity. Thus, they are a good thrombolytic agent having an action mechanism different from those of urokinase and streptokinase. It has been confirmed that using a synthetic chromophoric substrate, the plasminogen activator activity of SAK-11 is increased by addition of thrombin or by formation of fibrin, like SAK, and is compared with that of SAK with with respect to the intensity of the activity.

1 mg/ml of SAK-11 (or SAK) solution (20 mM phosphate buffer (pH 6.5) containing 0.01% of Tween 80) was diluted with the same buffer as set out above to prepare sample solutions of SAK-11 with different concentrations, for which an immmunoplate including 96 wells was provided. These solutions were, respectively, poured into four wells each in an amount of 8 microliter for each concentration. Among the four wells each having 8 microliter of the SAK-11 solution, 8 microliter of ion-exchanged water was added to the two wells for use as a control. 8 microliter of a 20U/m human thrombin (Sigma Co., Ltd.) solution (final concentration of thrombin of 2.5 U/ml) was added to the other wells. After mixing in a mixer, a mixture (144 microliter in total) of 8 microliter of human plasma, 8 microliter of S-2251 (KABI Co., Ltd.) and 128 microliter of a 50 mM tris-hydrochloride buffer (pH 7.4) containing 0.01% of Tween 80 was added to all the wells, followed by heating at 37 ° C. for 30 minutes. After completion of the heating, 40 microliter of 8% citric acid was added to each solution to stop the reaction, followed by measurement of absorbance at a wavelength of 405 nm.

Figure 7:
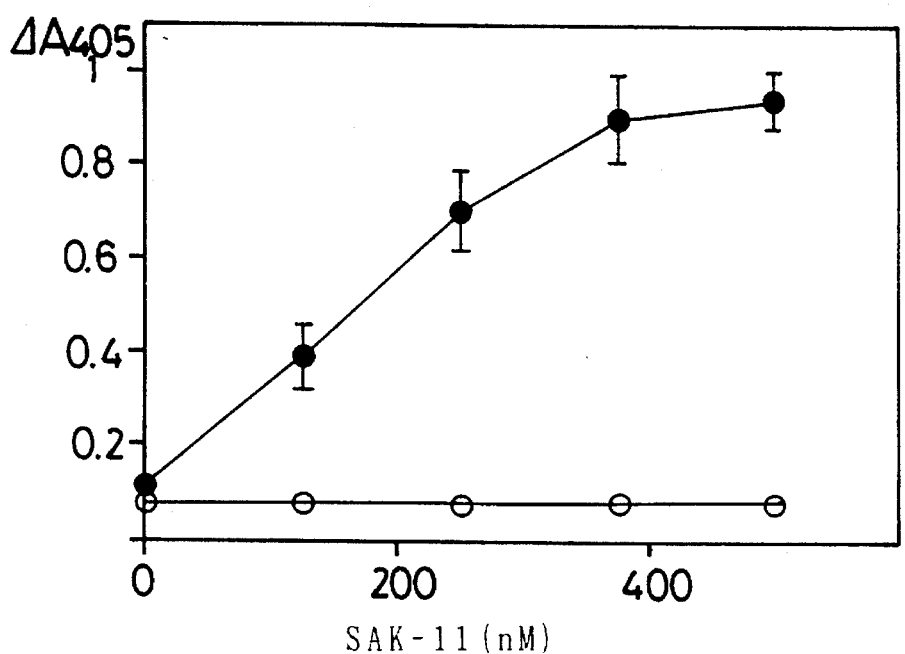
FIG. 7 is a graph showing the intensity of the plasminogen activation reaction at different concentrations of SAK-11.
Figure 8:
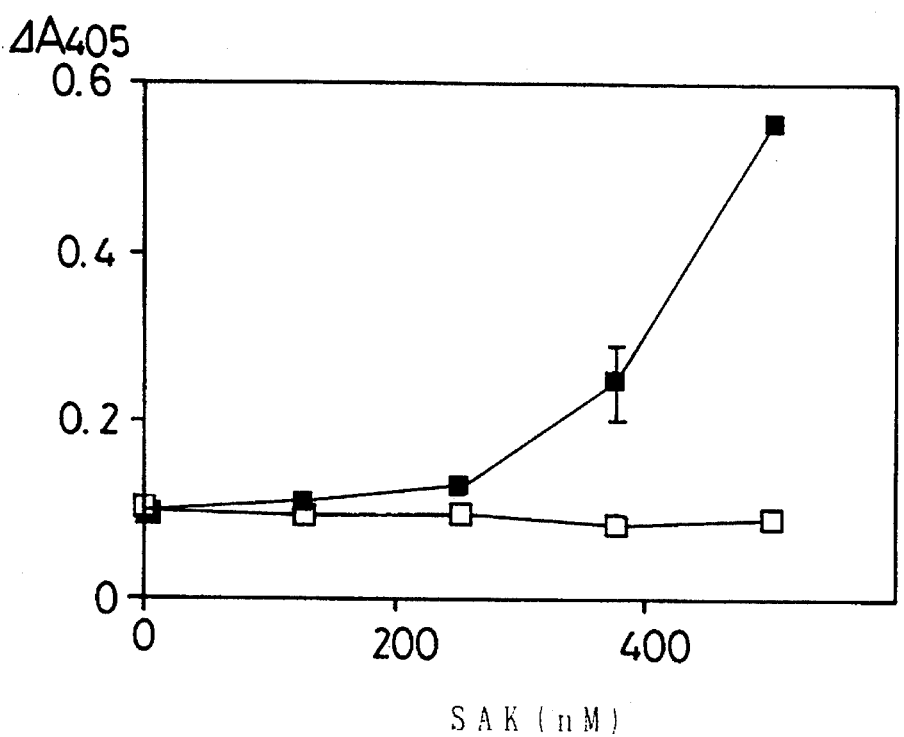
FIG. 8 is a graph showing the intensity of the plasminogen activation reaction at different concentrations of SAK.

FIG. 7 is a graph showing the intensity of the plasminogen activation reaction at different concentrations of SAK-11. In the figure, the ordinates indicates the variation of absorbance ($\Delta A_{405}$) and the abscissa indicates the concentration of SAK-11. The mark "○" indicates a control and the mark "●" indicates the case where 20 U/ml of thrombin was added. FIG. 8 is a graph showing the intensity of the plasminogen activation reaction at different concentrations of SAK. In the figure, the ordinates indicates the variation of absorbance ($\Delta A_{405}$) and the abscissa indicates the concentration of SAK. The mark "□" indicates a control and the mark "■" indicates the case where 20 U/ml of thrombin was added. As shown in FIGS. 7 and 8, it has been confirmed that like SAK, the plasminogen activation reaction of SAK-11 is increased by the action of thrombin. It has also been confirmed that on comparison with SAK, SAK-11 has a maximum activity at a lower concentration and exhibits a better specific activity than SAK, i.e. the same level of the activity is attained at a concentration of a fraction of SAK.

8. Safety Test of SAK-11 (Antigenic Test Using Mice):

The antigenicity of SAK-11 was determined, using an antibody productivity as an index, by providing streptokinase (SK) and egg-white albumin (OA) as a control and using BALB/c mice. As for the sensitivity of mice, there were provided two groups, one group being an adjuvant sensitization group wherein mice were intracelially sensitized twice at a dosage of 10 micrograms/mouse of aluminium hydroxide gel used as the adjuvant at intervals of three weeks. The other group was a clinically applied line sensitization group wherein mice were intravenously sensitize d at a dosage of 2 mg/kg three times but once a week. The IgE antibody productivity was checked by subjecting, to rat PCA reaction, the sensitized serum of blood collected one week after the final sensitization.

The SAK-induced PCA reaction of the SAK-sensitized mouse serum was negative for both adjuvant sensitization group and clinically applied line sensitization group. However, with the SK-sensitized mouse serum, one specimen of the clinically applied line sensitization group exhibited a positive reaction of the PCA value which is five times larger. The average PCA value of the pool serum of the adjuvant sensitization group of OA which was a positive control was by a factor of 245, showing a good reaction. With the sensitization group wherein OA was intravenously dosed, one specimen exhibited a positive reaction with the PCA value being 10 times larger.

From the foregoing results, the antigenicity of SAK using the IgE antibody productivity as an index has been found to be weaker than SK. In general toxicological observations after intravenous administration of 5 mg/body of rat (about 10 mg/kg) and 2 mg/kg of mouse, any specific change resulting from the doses was not recognized. The results suggested that SAK did not have such serious toxicity that troubles would be expected in clinical use.

9. Thrombolytic Agent (Use and Dosage):

The thrombolytic agent of the invention is a peptide soluble in water and is used as a preparation such as of injections and a contraceptive or remedy such as for various thromboses, intravascular coagulapathy, mycocardial infarction, walnut brain and the like.

For the preparation of the thrombolytic agent of the invention, various additives such as an excipient, a solubilizer, a stabilizer, a pH adjuster, an osmotic adjuster, an antioxidant and the like may be added within a range not impeding the efficacy of the agent.

The preparation may be supplied either as a physiological saline solution or as a freeze dried product which is employed by dissolution in distilled water for injection or in physiological saline on use.

The agent is generally dosed at one unit of 0.1 to 500 mg once or plural times, depending on the age, the sex, the weight and the symptoms. As a matter of course, in order to obtain a milder or more intense effect, it is possible to dose the agent in amounts exceeding the above range. Further, the manner of the administration depends on the type of preparation and includes, for example, intravenous administration, intraarterial administration, and direct administration to the affected part.

Specific examples of the preparations are set out in Tables 5 and 6 below.

TABLE 5

| Ingredients | Amount |
| --- | --- |
| SAK-11 | 10 mg |
| Maltose | 500 mg |
| Human alubmin | 1 g |
| monosodium-phosphate | 1.12 mg |
| disodium-phosphate | 1.33 mg |
| NaCl | 1.2 mg |

TABLE 6

| Ingredients | Amount |
| --- | --- |
| SAK-11 | 1 mg |
| Maltose | 500 mg |
| Human albumin | 1 g |
| monosodium-phosphate | 1.12 mg |
| disodium-phosphate | 1.33 mg |
| NaCl | 1.2 mg |

Table 5 shows an example of a freeze-dried preparation. The individual ingredients in the table is dissolved in 5 ml of distilled water for injection and filled in a sterile vial, followed by freeze-drying to obtain an injection vial.

Table 6 shows an example of an injection ampoule wherein the ingredients are dissolved in distilled water for injection and filled in a sterile ampoule to obtain an ampoule for injection.

We claim:

1. A thrombolytic agent comprising as its effective ingredient a peptide consisting of the amino acid sequence of SEQ ID NO: 2:

Lys—Gly—Asp—Asp—Ala—Ser—Tyr—Phe—Glu—Pro—
Thr—Gly—Pro—Tyr—Leu—Met—Val—Asn—Val—Thr—Gly—
Val—Asp—Gly—Lys—Gly—Asn—Glu—Leu—Leu—Ser—Pro—
His—Tyr—Val—Glu—Phe—Pro—Ile—Lys—Pro—Gly—Thr—
Thr—Leu—Thr—Lys—Glu—Lys—Ile—Glu—Tyr—Tyr—Val—
Glu—Trp—Ala—Leu—Asp—Ala—Thr—Ala—Tyr—Lys—Glu—
Phe—Arg—Val—Val—Glu—Leu—Asp—Pro—Ser—Ala—Lys—
Ile—Glu—Val—Thr—Tyr—Tyr—Asp—Lys—Asn—Lys—Lys—
Lys—Glu—Glu—Thr—Lys—Ser—Phe—Pro—Ile—Thr—Glu—
Lys—Gly—Phe—Val—Val—Pro—Asp—Leu—Ile—Glu—His—
Ile—Lys—Asn—Pro—Gly—Phe—Asn—Leu—Ile—Thr—Lys—
Val—Val—Ile—Glu—Lys—Lys.

2. A peptide having the amino acid sequence of sequence ID No: 2.

3. A thrombolytic agent comprising as an active ingredient the peptide of claim 2.

4. A thrombolytic agent according to claim 3, in which the activity of the peptide, as measured by a plasminogen activation reaction comprising measuring the variation in absorbance ($\Delta A_{405}$) when the agent is reacted with plasma, synthetic chromophoric substrate, and thrombin, is greater than about 0.2 $\Delta A_{405}$ at 200 nM and greater than about 0.4 $\Delta A_{405}$ at 400 nM.

5. A thrombolytic agent according to claim 3, further comprising a pharmaceutically acceptable amount of an additive selected from the group consisting of an excipient, a solubilizer, a stabilizer, a pH adjuster, an osmotic adjuster, an antioxidant, and combinations thereof.

6. A thrombolytic agent according to claim 3 in freeze-dried form.

7. A thrombolytic agent according to claim 3 further comprising physiological saline.

8. A thrombolytic agent according to claim 3 in single dosage form containing from about 0.1 mg to about 500 mg.

9. An injection ampoule comprising a unit dosage of the thrombolytic agent according to claim 3 with water in a sterile ampoule.

10. A thrombolytic formulation comprising as an active ingredient an essentially pure thrombolytic peptide obtained by proteolytically removing ten N-terminal amino acid residues from staphlyokinase, the thrombolytic peptide having at least 50 percent higher plasminogen activation activity than staphylokinase, as measured by an absorbance test using plasma, a chromophore, and thrombin.

11. The formulation of claim 10 in which the activity of the thrombolytic peptide is at least double that of staphylokinase.

12. The formulation of claim 10 in which the activity of the thrombolytic peptide is about four times that of staphylokinase.

13. The formulation of claim 10 in which the activity of the thrombolytic peptide reaches a maximum at less than about 400 nM.

14. An essentially pure peptide produced by cleaving off and removing ten amino acid residues from the N-terminal end of staphylokinase.

15. The peptide of claim 14, in which the peptide has a higher specific activity than staphlyokinase, and maximum thrombolytic activity at a concentration lower than staphylokinase.

16. A thrombolytic agent comprising as an active ingredient the peptide of claim 17.

17. A thrombolytic agent according to claim 16 in which the peptide is produced by a protease selected from the group consisting of trypsin, plasminogen, plasmin, and lysyl endopeptidase.

18. A thrombolytic agent according to claim 16 in which the peptide is produced by plasminogen or plasmin.

19. A thrombolytic agent according to claim 16, further comprising a pharmaceutically acceptable amount of an additive selected from the group consisting of an excipient, a solubilizer, a stabilizer, a pH adjuster, an osmotic adjuster, an antioxidant, and combinations thereof.

20. A thrombolytic agent according to claim 16 in freeze-dried form.

21. A thrombolytic agent according to claim 16 further comprising physiological saline.

22. A thrombolytic agent according to claim 16 in single dosage form containing from about 0.1 mg to about 500 mg.

23. An injection ampoule comprising a unit dosage of the thrombolytic agent according to claim 16 with water in a sterile ampoule.

* * * * *